(12) United States Patent
Peng (10) Patent No.: US 11,666,071 B2
(45) Date of Patent: *Jun. 6, 2023

(54) COMPOUND SALT OF N,N-DIMETHYLGLYCINE AND AN ORGANIC ACID AND COMPOSITION AND USE THEREOF

(71) Applicant: GUANGZHOU INSIGHTER BIOTECHNOLOGY CO., LTD., Guangdong (CN)

(72) Inventor: Xianfeng Peng, Guangzhou (CN)

(73) Assignee: GUANGZHOU INSIGHTER BIOTECHNOLOGY CO., LTD., Guangdong (CN)

( * ) Notice: Subject to any disclaimer, the term of this patent is extended or adjusted under 35 U.S.C. 154(b) by 374 days.

This patent is subject to a terminal disclaimer.

(21) Appl. No.: 16/754,758

(22) PCT Filed: Oct. 25, 2017

(86) PCT No.: PCT/CN2017/107673
§ 371 (c)(1),
(2) Date: Apr. 9, 2020

(87) PCT Pub. No.: WO2019/080009
PCT Pub. Date: May 2, 2019

(65) Prior Publication Data
US 2020/0296994 A1 Sep. 24, 2020

(51) Int. Cl.
*A23K 20/142* (2016.01)
*A23K 20/24* (2016.01)
(Continued)

(52) U.S. Cl.
CPC .......... *A23K 20/142* (2016.05); *A23K 20/105* (2016.05); *A23K 20/111* (2016.05); *A23K 20/24* (2016.05)

(58) Field of Classification Search
CPC .................................................... A23K 20/142
See application file for complete search history.

(56) References Cited

U.S. PATENT DOCUMENTS 8,523,975 B2 * 9/2013 Ettlin .................. C07F 3/003
71/33
2010/0183580 A1 7/2010 Kalmar et al.
(Continued)

FOREIGN PATENT DOCUMENTS

WO WO-2007107184 A1 * 9/2007 ........... A23K 20/142

OTHER PUBLICATIONS

International Search Report of PCT/CN2017/107673.
(Continued)

*Primary Examiner* — Changqing Li
(74) *Attorney, Agent, or Firm* — Kam Wah Law (57) ABSTRACT

The present invention discloses a polyvalent metal ion compound salt of N,N-dimethylglycine and organic acid or a solvate thereof, and use thereof in preparing novel feed additives and feed; the present invention also discloses a composition comprising the polyvalent metal ion compound salt of N,N-dimethylglycine and organic acid or the solvate thereof. The polyvalent metal ion compound salt of N,N-dimethylglycine and organic acid or the solvate thereof provided by the present invention has improvement effect on animal product performance such as improving animal weight gain and reducing feed conversion ratio, showing effects similar to or higher than that of sodium N,N-dimethylglycinate.

20 Claims, 1 Drawing Sheet (51) Int. Cl.
*A23K 20/105* (2016.01)
*A23K 20/111* (2016.01)

(56) References Cited

U.S. PATENT DOCUMENTS

2014/0316004 A1  10/2014  Janssens et al.
2020/0297675 A1* 9/2020  Peng .................... C07C 227/18

OTHER PUBLICATIONS

International Written Opinion of PCT/CN2017/107673.
Sun, Yongtai, "Application of anti-mildew agent in feed production," Jiangxi Feed, Dec. 30, 2015 (Dec. 30, 2015), No. 02.
English Translation of the Abstract of Sun, Yongtai.
Long, Shenfei et al., "A Review on Application Effect and Mechanism of Organic Acids (Salts) in Pig Production," Swine Production, Dec. 30, 2016 (Dec. 30, 2016), No. 06.

* cited by examiner

COMPOUND SALT OF N,N-DIMETHYLGLYCINE AND AN ORGANIC ACID AND COMPOSITION AND USE THEREOF

CROSS-REFERENCE TO RELATED APPLICATIONS

This is a U.S. national stage application of the International Patent Application No. PCT/CN2017/107673, filed Oct. 25, 2017, which is incorporated herein by reference in its entirety.

FIELD OF THE INVENTION

The present invention relates to the field of animal feed additives, and particularly relates to a compound salt of N,N-dimethylglycine or a solvate thereof, and a composition comprising the salt, and use thereof in preparing animal feed additives.

BACKGROUND OF THE INVENTION

Dimethylglycine (DMG), with a molecular formula as $(CH_3)_2NCH_2COOH$, is white crystals, and soluble in water and ethanol. It is a physiologically active nutrient that naturally occurs in food, grains, beans and liver, and is a natural substance occurring in the metabolic pathways of plants and animals. As a nutritional antioxidant additive, dimethylglycine also shows important physiological and biochemical functions in human and animal health. It has been found in a large number of animal tests that dimethylglycine is a very safe food-based nutritional additive.

However, N,N-dimethylglycine is a highly hygroscopic solid, which is difficult to store and use. The commonly used N,N-dimethylglycine hydrochloride, sodium N,N-dimethylglycinate and potassium N,N-dimethylglycinate also show strong hygroscopicity, and are prone to absorb moisture and deliquesce during storage; thus, high requirements on production equipment and plant facilities shall be established in the product processing, or otherwise the products will absorb moisture and thus agglomerate during the production, failing to meet the application requirements of the feed processing industry. In addition, the packaging of products containing DMG or DMG hydrochloride or alkali metal salt must be tightly sealed; with poor sealing, the product will get moldy and deteriorate due to moisture absorption during storage.

SUMMARY OF THE INVENTION

Provided herein is a polyvalent metal ion compound salt of N,N-dimethylglycine and an organic acid, comprising a N,N-dimethylglycinate ion, a polyvalent metal ion in an amount equimolar to the N,N-dimethylglycinate ion, wherein an ion of the organic acid is acceptable for a feed, and in an amount equal to chemical equivalents of the N,N-dimethylglycinate ion and the polyvalent metal ion. Also provided herein is a feed composition, comprising at least one of the polyvalent metal ion compound disclosed herein or a solvate thereof and an auxiliary material usable for feed. Also provided herein is use of the polyvalent metal ion compound salt disclosed herein or the feed composition disclosed herein in preparing an animal feed additive or an animal feed.

DETAILED DESCRIPTION OF THE INVENTION

In view of the above, the present invention provides a N,N-dimethylglycinate salt which is not prone to absorb moisture. The N,N-dimethylglycinate salt is a polyvalent metal ion compound salt of N,N-dimethylglycine and organic acid, or a solvate thereof, which has an animal-growth improvement effect equivalent to or better than that of sodium N,N-dimethylglycinate. Particularly, the present invention also provides a feed composition comprising the polyvalent metal ion compound salt of N,N-dimethylglycine and organic acid or the solvate thereof, and the use of the composition and the polyvalent metal ion compound salt of N,N-dimethylglycine and organic acid or the solvate thereof in preparing animal feed additives or animal feed.

In one aspect, the present invention provides a polyvalent metal ion compound salt of N,N-dimethylglycine and organic acid or a solvate thereof, comprising a N,N-dimethylglycinate ion, a polyvalent metal ion in an amount equimolar to the N,N-dimethylglycinate ion, and a feed acceptable organic acid ion in an amount equal to chemical equivalents of the N,N-dimethylglycinate ion and the polyvalent metal ion.

In some embodiments, the polyvalent metal ion in the amount equimolar to the N,N-dimethylglycinate ion is a divalent metal ion or a trivalent metal ion.

In some embodiments, the divalent metal ion is an alkaline earth metal ion and may be selected from Ca(II), Mg(II), Ba(II), or Sr(II).

In some embodiments, the divalent metal ion is a transition metal divalent ion and may be selected from Cu(II), Zn(II), Fe(II), Mn(II), Cr(II), Cd(II), Co(II) or Ni(II).

In some embodiments, the trivalent metal ion may be selected from Al(III), Cr(III), or Fe(III).

In some embodiments, an organic acid corresponding to the organic acid ion is an organic polyacid, and may be selected from fumaric acid, maleic acid, tartaric acid, succinic acid, malonic acid, malic acid, dihydroxypropionic acid, pyruvic acid, glycolic acid, glucuronic acid, galacturonic acid, aspartic acid, glutamic acid, citric acid or oxalic acid.

In some embodiments, the organic acid corresponding to the organic acid ion is preferably fumaric acid.

In some embodiments, the organic acid corresponding to the organic acid ion is a linear fatty monoacid, and may be selected from a $C_4$-$C_{18}$ linear fatty monoacid.

In some embodiments, the organic acid corresponding to the organic acid ion is an aromatic organic acid, and may be selected from benzoic acid, p-toluic acid, p-chlorobenzoic acid, p-bromobenzoic acid, p-aminobenzoic acid, mandelic acid, cinnamic acid, benzenesulfonic acid, p-methylbenzenesulfonic acid, naphthoic acid, salicylic acid or acetylsalicylic acid.

In some embodiments, the organic acid corresponding to the organic acid ion is preferably benzoic acid or p-toluic acid.

In some embodiments, the polyvalent metal ion compound salt of N,N-dimethylglycine and organic acid comprises a N,N-dimethylglycinate ion, a Ca(II) ion in an amount equimolar to the N,N-dimethylglycinate ion, and a benzoate ion in an amount equal to chemical equivalents of the N,N-dimethylglycinate ion and the Ca(II) ion.

In some embodiments, the polyvalent metal ion compound salt of N,N-dimethylglycine and organic acid comprises a N,N-dimethylglycinate ion, a Ca(II) ion in an amount equimolar to the N,N-dimethylglycinate ion, and a fumarate ion in an amount equal to chemical equivalents of the N,N-dimethylglycinate ion and the Ca(II) ion.

In some embodiments, the polyvalent metal ion compound salt of N,N-dimethylglycine and organic acid comprises a N,N-dimethylglycinate ion, a Cu(II) ion in an amount equimolar to the N,N-dimethylglycinate ion, and a benzoate ion in an amount equal to chemical equivalents of the N,N-dimethylglycinate ion and the Cu(II) ion.

In some embodiments, the polyvalent metal ion compound salt of N,N-dimethylglycine and organic acid comprises a N,N-dimethylglycinate ion, a Cu(II) ion in an amount equimolar to the N,N-dimethylglycinate ion, and a fumarate ion in an amount equal to chemical equivalents of the N,N-dimethylglycinate ion and the Cu(II) ion.

In some embodiments, the polyvalent metal ion compound salt of N,N-dimethylglycine and organic acid comprises a N,N-dimethylglycinate ion, a Zn(II) ion in an amount equimolar to the N,N-dimethylglycinate ion, and a benzoate ion in an amount equal to chemical equivalents of the N,N-dimethylglycinate ion and the Zn(II) ion.

In some embodiments, the polyvalent metal ion compound salt of N,N-dimethylglycine and organic acid comprises a N,N-dimethylglycinate ion, a Zn(II) ion in an amount equimolar to the N,N-dimethylglycinate ion, and a fumarate ion in an amount equal to chemical equivalents of the N,N-dimethylglycinate ion and the Zn(II) ion.

In another aspect, the present invention provides a feed composition comprising at least one of the polyvalent metal ion compound salt of N,N-dimethylglycine and organic acid or the solvate thereof provided by the present invention and an auxiliary material usable for feed.

Optionally, the auxiliary material usable for feed is a carrier, a diluent, an excipient, a medium, or a combination thereof that is usable for feed.

In some embodiments, the feed composition further comprises a feed raw material and/or an additional animal feed additive.

Optionally, the additional animal feed additive is a nutritional feed additive, a general feed additive or a medicinal feed additive.

The present invention provides use of the polyvalent metal ion compound salt of N,N-dimethylglycine and organic acid or the solvate thereof.

In some embodiments, use of the polyvalent metal ion compound salt of N,N-dimethylglycine and organic acid in preparing animal feed additives.

In some embodiments, use of the polyvalent metal ion compound salt of N,N-dimethylglycine and organic acid in preparing animal feed.

The animal is a farmed animal, and is selected from livestock, poultry, aquaculture animals or pets.

The present invention provides use of the feed composition comprising the polyvalent metal ion compound salt of N,N-dimethylglycine and organic acid or the solvate thereof.

In some embodiments, use of the feed composition in preparing animal feed additives.

In some embodiments, use of the feed composition in preparing animal feed.

The animal is a farmed animal, and is selected from livestock, poultry, aquaculture animals or pets.

In another aspect, the present invention further provides a method for improving production performance of a farmed animal.

In some embodiments, the method comprises administering the polyvalent metal ion compound salt of N,N-dimethylglycine and organic acid or the solvate thereof provided by the present invention to a farmed animal alone with feed.

In some embodiments, the method comprises administering the feed composition comprising the polyvalent metal ion compound salt of N,N-dimethylglycine and organic acid or the solvate thereof provided by the present invention to a farmed animal.

In another aspect, the present invention further provides a method for preparing, isolating and purifying the polyvalent metal ion compound salt of N,N-dimethylglycine and organic acid.

The beneficial effects of the present invention:

The polyvalent metal ion compound salt of N,N-dimethylglycine and organic acid provided by the present invention is a salt formed by N,N-dimethylglycine and an organic acid simultaneously with a polyvalent metal ion, by which the hygroscopicity of N,N-dimethylglycine can be reduced. When the polyvalent metal ion compound salt of N,N-dimethylglycine and organic acid or the solvate thereof is applied in preparing animal feed additives or feed, the reduction in hygroscopicity makes it possible to lower the damp-proofing requirements on the production equipment of feed or feed additives and thus reduce the production cost. In addition, the reduction in hygroscopicity of products also lowers the sealing requirements on product packaging, which reduces the cost and avoid the risk of short-term moisture deterioration of the product due to packaging damage caused by accidents during transportation or storage.

In the breeding test, the polyvalent metal ion compound salt of N,N-dimethylglycine and organic acid provided by the present invention showed a improvement effect on the production performance of poultry and livestock equivalent to that of sodium N,N-dimethylglycinate, and some of salts even showed slightly better improvement effect.

Any embodiment of any aspect of the present invention may be combined with other embodiments as long as there is no contradiction therebetween. In addition, in any embodiment of any aspect of the present invention, any technical feature may be applied to the technical feature in other embodiments as long as there is no contradiction therebetween.

The foregoing has outlined, but is not limited to, certain aspects of the invention. The above-mentioned content and other aspects will be described in more detail below.

A further detailed description of the invention.

Certain embodiments of the invention will now be described in detail, examples of which are illustrated by the accompanying structural or chemical formulas. The invention is intended to cover all alternatives, modifications and equivalent technical solutions, which are all included within the scope of the invention as defined by the claims. In addition, in order to clearly illustrate, certain technical features of the present invention are described separately in multiple independent embodiments, but may also be provided in a single embodiment in a combination form or in any suitable combination.

The present invention provides a polyvalent metal ion compound salt of N,N-dimethylglycine and organic acid, comprising a N,N-dimethylglycinate ion, a polyvalent metal ion in an amount equimolar to the N,N-dimethylglycinate ion, and an feed acceptable organic acid ion in an amount equal to chemical equivalents of the N,N-dimethylglycinate ion and the polyvalent metal ion.

The term "comprise (or comprises, comprised, comprising)" in the present invention is open-ended, which includes the content explicitly referred to in the present invention, but does not exclude the content of other aspects.

The term "polyvalent metal ion" involved in the present invention refers to a metal ion having a valency of +2 or +3.

The term "in an amount equimolar to" involved in the present invention refers to that the number of the polyvalent metal ion is equal to the number of N, N-dimethylglycinate ion.

The term "in an amount equal to chemical equivalents of" involved in the present invention refers to that a total anion valency of the organic acid ion enables a compound containing the N,N-dimethylglycinate ion and polyvalent metal ion of the equimolar amount exhibits an electric neutrality status with a positive and negative charge equilibrium.

The term "feed acceptable organic acid ion" involved in the present invention refers to an organic acid ion suitable in term of chemistry or toxicology, related to the feed formed thereof or the farmed animals, and non-toxic to animals.

The term "compound salt" involved in the present invention refers to a salt composed of the N,N-dimethylglycinate ion and the other organic acid ion, which serve together as the anionic counterpart, with the metal ion.

A preparation method of the polyvalent metal ion compound salt of N,N-dimethylglycine and organic acid is as follows:

The N,N-dimethylglycine hydrochloride (referred to as DMG hydrochloride) undergoes a neutralization reaction in a lower alcohol organic solvent with a same chemical equivalent of an inorganic base to obtain free N,N-dimethylglycine, which is then evenly mixed with another organic acid at room temperature to obtain a reaction liquid; the reaction liquid further reacts, with an alkaline polyvalent metal hydroxide, or with a polyvalent metal halide under an alkaline condition, to form a corresponding polyvalent metal ion compound salt of N,N-dimethylglycine and organic acid, wherein the term "same chemical equivalent" refers to that an amount of the inorganic base enables to dissociate the DMG hydrochloride to obtain free DMG.

Optionally, the lower alcohol organic solvent is methanol, ethanol, n-propanol, i-propanol, or n-butanol.

In some embodiments, the inorganic base is aqueous ammonium or hydroxide, carbonate or bicarbonate of alkali metal, including but not limited to sodium hydroxide, potassium hydroxide, sodium carbonate, sodium bicarbonate, potassium carbonate and potassium bicarbonate.

In some embodiments, the other organic acid evenly mixed with the free DMG may be selected from an organic polyacid, a linear fatty monoacid or an aromatic organic acid.

The organic polyacid may be selected from fumaric acid, maleic acid, tartaric acid, succinic acid, malonic acid, malic acid, dihydroxypropionic acid, pyruvic acid, glycolic acid, glucuronic acid, galacturonic acid, aspartic acid, glutamic acid, citric acid or oxalic acid, and preferably fumaric acid.

The linear fatty monoacid may be selected from a $C_4$-$C_{18}$ linear fatty monoacid, and preferably tetradecanoic acid.

The term "$C_4$-$C_{18}$ linear fatty monoacid" involved in the present invention refers to a fatty monoacid having 4 to 18 carbon atoms without a branched chain.

The aromatic organic acid may be selected from benzoic acid, p-toluic acid, p-chlorobenzoic acid, p-bromobenzoic acid, p-aminobenzoic acid, mandelic acid, cinnamic acid, benzenesulfonic acid, p-methylbenzenesulfonic acid, naphthoic acid, salicylic acid or acetylsalicylic acid, and preferably benzoic acid, p-toluic acid or p-methylbenzenesulfonic acid.

In some embodiments, the alkaline polyvalent metal hydroxide, which reacts with the reaction liquid formed by evenly mixing the free DMG and the organic acid, may be selected from an alkaline divalent metal hydroxide or an alkaline trivalent metal hydroxide.

Optionally, the alkaline divalent metal hydroxide is an alkaline earth metal hydroxide. Specifically, the alkaline earth metal hydroxide is calcium hydroxide ($Ca(OH)_2$), magnesium hydroxide ($Mg(OH)_2$), barium hydroxide ($Ba(OH)_2$), or strontium hydroxide ($Sr(OH)_2$), and the metal ion contained in the corresponding product polyvalent metal ion compound salt of N,N-dimethylglycine and organic acid is a divalent alkaline earth metal ion, which may be selected from Ca(II), Mg(II), Ba(II) or Sr(II).

Further optionally, the alkaline divalent metal hydroxide is an alkaline transition metal hydroxide. Specifically, the alkaline transition metal hydroxide is copper hydroxide ($Cu(OH)_2$), zinc hydroxide ($Zn(OH)_2$), ferrous hydroxide ($Fe(OH)_2$), cadmium hydroxide ($Cd(OH)_2$), cobalt hydroxide ($Co(OH)_2$) or nickel Hydroxide ($Ni(OH)_2$), and the metal ion contained in the corresponding product polyvalent metal ion compound salt of N,N-dimethylglycine and organic acid is a divalent transition metal ion, which may be selected from Cu(II), Zn(II), Fe(II), Cd(II), Co(II) or Ni(II).

In some embodiments, the alkaline polyvalent metal hydroxide, which reacts with the reaction liquid formed by evenly mixing the free DMG and the organic acid, is an alkaline trivalent metal hydroxide, the alkaline trivalent metal hydroxide is preferably selected from iron hydroxide ($Fe(OH)_3$), chromium hydroxide ($Cr(OH)_3$), or aluminum hydroxide ($Al(OH)_3$), and the metal ion contained in the corresponding product polyvalent metal ion compound salt of N,N-dimethylglycine and organic acid is a trivalent metal ion, which may be selected from Al(III), Cr(III) or Fe(III).

In some embodiments, the polyvalent metal halide, which reacts with the reaction liquid formed by evenly mixing the free DMG and the organic acid, may be selected from a polyvalent metal chloride, a polyvalent metal bromide, or a polyvalent metal iodide.

The alkaline condition refers to that sufficient sodium hydroxide is added to the reaction system so that the pH value of the reaction system is 7 to 8.

The polyvalent metal chloride is specifically Copper Chloride ($CuCl_2$), zinc chloride ($ZnCl_2$), manganese chloride ($MnCl_2$), ferrous chloride ($FeCl_2$), ferric chloride ($FeCl_3$), chromous chloride ($CrCl_2$), chromium chloride ($CrCl_3$), cadmium chloride ($CdCl_2$), cobalt chloride ($CoCl_2$) or nickel chloride ($NiCl_2$).

The polyvalent metal bromide is specifically copper bromide ($CuBr_2$), zinc bromide ($ZnBr_2$), manganese bromide ($MnBr_2$), ferrous bromide ($FeBr_2$), iron bromide ($FeBr_3$), chromous bromide ($CrBr_2$), chromium bromide ($CrBr_3$), cadmium bromide ($CdBr_2$), cobalt bromide ($CoBr_2$) or nickel bromide ($NiBr_2$).

The polyvalent metal iodide is specifically copper bromide ($CuI_2$), zinc iodide ($ZnI_2$), manganese iodide ($MnI_2$), iron iodide ($FeI_2$), iron iodide ($FeI_3$), chromous iodide ($CrI_2$), chromium iodide ($CrI_3$), cadmium iodide ($Cd_2$), cobalt iodide ($CoI_2$) or nickel iodide ($NiI_2$).

The metal ion, contained in the corresponding product polyvalent metal ion compound salt of N,N-dimethylglycine and organic acid formed in the above process, is Cu(II), Zn(II), Fe(II), Mn(II), Cr(II), Cd(II), Co(II), Ni(II), Cr(III) or Fe(III).

In one specific embodiment, the DMG hydrochloride undergoes a neutralization reaction in absolute ethanol with a same chemical equivalent of sodium hydroxide to obtain free N,N-dimethylglycine, which is then evenly mixed with benzoic acid at room temperature to obtain a reaction liquid; the reaction liquid further reacts with powdery calcium hydroxide to form the corresponding calcium salt of N,N-dimethylglycine and benzoic acid. The calcium salt of N,N-dimethylglycine and benzoic acid comprises a N,N-dimethylglycinate ion, a Ca(II) ion in an amount equimolar to the N,N-dimethylglycinate ion, and a benzoate ion in an amount equal to chemical equivalents of the N,N-dimethylglycinate and the Ca(II) ion.

In one specific embodiment, the DMG hydrochloride undergoes a neutralization reaction in absolute ethanol with a same chemical equivalent of sodium hydroxide to obtain free N,N-dimethylglycine, which is then evenly mixed with fumaric acid at room temperature to obtain a reaction liquid; the reaction liquid further reacts with powdery calcium hydroxide to form the corresponding calcium salt of N,N-dimethylglycine and fumaric acid. The calcium salt of N,N-dimethylglycine and fumaric acid comprises a N,N-dimethylglycinate ion, a Ca(II) ion in an amount equimolar to the N,N-dimethylglycinate ion, and a fumarate ion in an amount equal to chemical equivalents of the N,N-dimethylglycinate ion and the Ca(II) ion.

In one specific embodiment, the DMG hydrochloride undergoes a neutralization reaction in absolute ethanol with a same chemical equivalent of sodium hydroxide to obtain free N,N-dimethylglycine, which is then evenly mixed with benzoic acid at room temperature to obtain a reaction liquid; the reaction liquid further reacts with powdery copper hydroxide to form the corresponding copper salt of N,N-dimethylglycine and benzoic acid. The copper salt of N,N-dimethylglycine and benzoic acid comprises a N,N-dimethylglycinate ion, a Cu(II) ion in an amount equimolar to the N,N-dimethylglycinate ion, and a benzoate ion in an amount equal to chemical equivalents of the N,N-dimethylglycinate ion and the Cu(II) ion.

In one specific embodiment, the DMG hydrochloride undergoes a neutralization reaction in absolute ethanol with a same chemical equivalent of sodium hydroxide to obtain free N,N-dimethylglycine, which is then evenly mixed with fumaric acid at room temperature to obtain a reaction liquid; the reaction liquid further reacts with powdery copper hydroxide to form the corresponding copper salt of N,N-dimethylglycine and fumaric acid. The copper salt of N,N-dimethylglycine and fumaric acid comprises a N,N-dimethylglycinate ion, a Cu(II) ion in an amount equimolar to the N,N-dimethylglycinate ion, and a fumarate ion in an amount equal to chemical equivalents of the N,N-dimethylglycinate ion and the Cu(II) ion.

In one specific embodiment, the DMG hydrochloride undergoes a neutralization reaction in absolute ethanol with a same chemical equivalent of sodium hydroxide to obtain free N,N-dimethylglycine, which is then evenly mixed with fumaric acid at room temperature to obtain a reaction liquid; the reaction liquid further reacts with powdery zinc hydroxide to form the corresponding zinc salt of N,N-dimethylglycine and fumaric acid. The zinc salt of N,N-dimethylglycine and fumaric acid comprises a N,N-dimethylglycinate ion, a Zn(II) ion in an amount equimolar to the N,N-dimethylglycinate ion, and a fumarate ion in an amount equal to chemical equivalents of the N,N-dimethylglycinate ion and the Zn(II) ion.

In one specific embodiment, the DMG hydrochloride undergoes a neutralization reaction in absolute ethanol with a same chemical equivalent of sodium hydroxide to obtain free N,N-dimethylglycine, which is then evenly mixed with benzoic acid at room temperature to obtain a reaction liquid; the reaction liquid further reacts with powdery zinc hydroxide to form the corresponding zinc salt of N,N-dimethylglycine and benzoic acid. The zinc salt of N,N-dimethylglycine and benzoic acid comprises a N,N-dimethylglycinate ion, a Zn(II) ion in an amount equimolar to the N,N-dimethylglycinate ion, and a benzoate ion in an amount equal to chemical equivalents of the N,N-dimethylglycinate ion and the Zn(II) ion.

In some embodiments, the preparation process of the polyvalent metal ion compound salt of N,N-dimethylglycine and organic acid provided by the present invention further involves the separation, purification or recrystallization process of the reaction product.

In order to obtain a polyvalent metal ion compound salt of N,N-dimethylglycine and organic acid with higher chemical purity and lower impurity content, the crude product is recrystallized under appropriate temperature, illumination and mechanical vibration conditions with an alcohol solvent, an alcohol-water mixed solvent or other organic solvents that can be used for product recrystallization, and separated to obtain a polyvalent metal ion compound salt of N,N-dimethylglycine and organic acid with a certain crystalline state. The said polyvalent metal ion compound salt of N,N-dimethylglycine and organic acid with a certain crystalline state may be a solvate thereof.

The term "solvate" involved in the present invention refers to a co-crystallizing complex formed by the compound salt combining with solvent molecules in a chemical equivalent or non-chemical equivalent amount through non-covalent intermolecular forces caused by external conditions and internal conditions during the process of contacting the compound salt with the solvent molecules. Solvents for forming the solvate include but not limited to water, acetone, ethanol, methanol, dimethyl sulfoxide, ethyl acetate, acetic acid, and i-propanol. "Hydrate" refers to a complex or crystal formed when the solvent molecules are water, i.e., a compound formed by combining with water in a chemical equivalent or non-chemical equivalent amount through non-covalent intermolecular forces.

A solvate of the polyvalent metal ion compound salt of N,N-dimethylglycine and organic acid may be selected from a hydrate or ethanolate of the polyvalent metal ion compound salt of N,N-dimethylglycine and organic acid.

The present invention provides a high-humidity stability study of the above-mentioned polyvalent metal ion compound salts of N,N-dimethylglycine and organic acid. In the high-humidity stability test study prescribed by the new stability test standard for feed additives, the polyvalent metal ion compound salts of N,N-dimethylglycine and organic acid were placed at 25° C. and RH 95% and all showed a hygroscopic weight gain of less than 5% at day 10, satisfying the requirements of feed additives on humidity.

The present invention provides a feed composition, comprising at least one of the polyvalent metal ion compound salts of N,N-dimethylglycine and organic acid or the solvate thereof provided by the present invention and an auxiliary material usable for feed.

The term "composition" involved in the present invention refers to a collective of compounds including one or more compounds as an active ingredient.

Optionally, the auxiliary material usable for feed includes a feed additive or a carrier, a binder, an anti-caking agent, a stabilizer, an emulsifier, a diluent, a medium, or a combination thereof that is commonly used in feed.

The term "carrier" involved in the present invention refers to a substance useable in feed and capable of carrying an active ingredient, improving dispersibility thereof, and having high chemical stability and adsorption, and includes organic carriers or inorganic carriers. The organic carriers are generally materials containing a lot of crude fibers, including but not limited to corn flour, corn cob flour, wheat bran, rice hull flour, defatted rice bran, rice bran and hull, corn stalk flour, and peanut hull flour. The inorganic carriers are generally minerals, mainly include calcium salts and silicon oxides, and are used for the preparation of trace element premixes, including but not limited to calcium carbonate, silicate, vermiculite, zeolite, and sepiolite.

The term "diluent" involved in the present invention refers to a substance that evenly distributes additive raw materials in other materials, and dilutes high-concentration additive raw materials into low-concentration premixed agents or premixes; it can separate trace components from each other and reduce the interaction between active ingredients, so as to increase the stability of the active ingredients without affecting the physical and chemical properties thereof. Diluents include organic diluents and inorganic diluents. Common organic diluents include, but are not limited to, corn flour, degermed corn flour, dextrose (glucose), sucrose, semolina with bran, stir-fried soybean powder, wheat middling, and corn gluten meal. Commonly used inorganic diluents include but are not limited to limestone, calcium dihydrogen phosphate, shell powder, kaolin (white clay), salt and sodium sulfate.

Auxiliary agents involved in the present invention include, but are not limited to, binders, wetting agents, disintegrants, lubricants, antioxidants, and preservatives.

The term "medium" involved in the present invention refers to solvents required for dissolving or dispersing solids, which include, but are not limited to, water, ethanol, and glycerin.

Further, the feed composition comprises an additional animal feed additive, and the additional animal feed is selected from a nutritional feed additive, a general feed additive or a medicinal feed additive.

Specifically, the nutritional feed additive includes, but is not limited to, amino acids, amino acid salts and their analogues, vitamins and vitamin-like substances, mineral elements and their complexes (chelates), microbial enzyme preparations, or non-protein nitrogen; the general feed additive includes, but is not limited to, growth promoters, deworming agents, flavorings and attractants, feed conditioning agents, feed conditioners, feed preservatives, and Chinese herbal medicine additives; the medicinal feed additive includes, but is not limited to, a veterinary drug premix which has the function of preventing animal diseases and promoting animal growth and can be added to the feed for a long period of time and incorporated into a carrier or diluent.

Further, the feed composition may include a feed raw material, the feed raw material being selected from animal, plant, microbial and mineral non-feed-additive substances that are usable for feed and can be used to prepare feed.

In some embodiments, the feed composition is an additive-premixed feed, a concentrated feed, a compound feed, or a concentrate supplement.

The additive-premixed feed refers to a uniform mixture prepared by mixing nutritional feed additive, which comprises any two or more of mineral trace elements, vitamins, microorganisms, and amino acids, with the polyvalent metal ion compound salt provided by the present invention or other feed additives, carriers and/or diluents according to a certain proportion, wherein the nutritional feed additive is present in a content that can meet the basic nutritional requirements of an applicable animal within its specific physiological stage, and is not less than 0.1% and not more than 10% in the compound feed, concentrate supplement or animal drinking water.

The concentrated feed refers to a feed mainly composed of proteins, minerals and feed additives according to a certain proportion.

The compound feed refers to a feed prepared by mixing a variety of feed raw materials and feed additives according to a certain proportion depending on the nutritional needs of the farmed animals.

The concentrate supplement refers to a feed prepared by mixing a variety of feed raw materials and feed additives according to a certain proportion in order to supplement nutrition to herbivores.

The invention also involves a preparation process of the feed composition, comprising weighing the raw materials and auxiliary materials, mixing by a mixing unit, granulating, quality inspection and packaging.

The present invention involves the use of the above-mentioned polyvalent metal ion compound salt of N,N-dimethylglycine and organic acid and the feed composition comprising the polyvalent metal ion compound salt of N,N-dimethylglycine and organic acid in preparing animal feed additives or animal feed.

The term "animal" involved in the present invention refers to human or farmed animals that cannot synthesize organic matters from inorganic matters, but can only utilize organic matters as food in order to perform vital activities such as ingestion, digestion, absorption, breathing, circulation, excretion, sensation, exercise, and reproduction.

Optionally, the farmed animals include poultry, livestock, aquatic animals, and other farmed and legally captured animals including pets. Specifically, the poultry involved in the present invention are edible animals such as chicken, ducks, geese, pigeons, quails or turkeys at various growth stages; the livestock involved in the present invention are edible animals such as pigs, cattle, sheep, rabbits, and horses at various growth stages; the aquatic animals involved in the present invention are fish, shrimps, loaches, crabs or eels at each growth stage; the pets involved in the present invention include, but are not limited to, cats, dogs, and rabbits.

In some breeding schemes, addition of the polyvalent metal ion compound salt of N,N-dimethylglycine and organic acid provided by the present invention into the basal feed of poultry such as chicken, ducks, geese or pigeons, can significantly reduce the feed conversion ratio and improve the feed efficiency for poultry, showing an effect equivalent to that of N,N-dimethylglycine.

In some breeding schemes, addition of the polyvalent metal ion compound salt of N,N-dimethylglycine and organic acid provided by the present invention into the basal feed of monogastric or ruminant livestock such as pigs, cattle, and sheep, shows significant improvement effect on the production performance of the livestock, which is illustrated by the average daily weight gain and decrease in average feed conversion ratio.

In some breeding schemes, addition of the polyvalent metal ion compound salt of N,N-dimethylglycine and organic acid provided by the present invention into the basal feed of aquatic animals such as fish and shrimps, can significantly improve anoxic resistance and survival rate of the aquatic animals, especially fish.

In some breeding schemes, a low level of copper salt of N,N-dimethylglycine and organic acid provided by the present invention in the basal feed of farmed animals shows an improvement effect on animal production performance similar to that of a high level of inorganic copper additive.

In some breeding schemes, addition of the zinc salt of N,N-dimethylglycine and organic acid provided by the present invention into the basal feed of farmed animals can significantly improve production performance of the animals.

In some breeding schemes, the polyvalent metal ion compound salts of N,N-dimethylglycine and organic acid can be applied in combination with pet food such as cat food and dog food to realize the effect of regulating the gastrointestinal function of pets such as cats and dogs and effectively relieve diarrhea symptoms caused by indigestion in pets.

Therefore, the non-hygroscopic polyvalent metal ion compound salts of N,N-dimethylglycine and organic acid meet the requirements of novel feed additives for high humidity stability and present an improvement effect on the production performance of farmed animals similar to or higher than that of sodium N,N-dimethylglycinate, thus can be used in the preparation of animal feed additives or animal feed.

Further, the copper salts of N,N-dimethylglycine and organic acid and the zinc salts of N,N-dimethylglycine and organic acid can respectively be used as a substitute for high-level inorganic copper additive and high-level inorganic zinc additive in the preparation of animal feed additives or animal feed, in the feed additive or feed processing industry.

The feed involved in the present invention refers to an industrially processed and produced product used as food for animals.

DETAILED DESCRIPTION OF THE EMBODIMENTS

Figure 1:
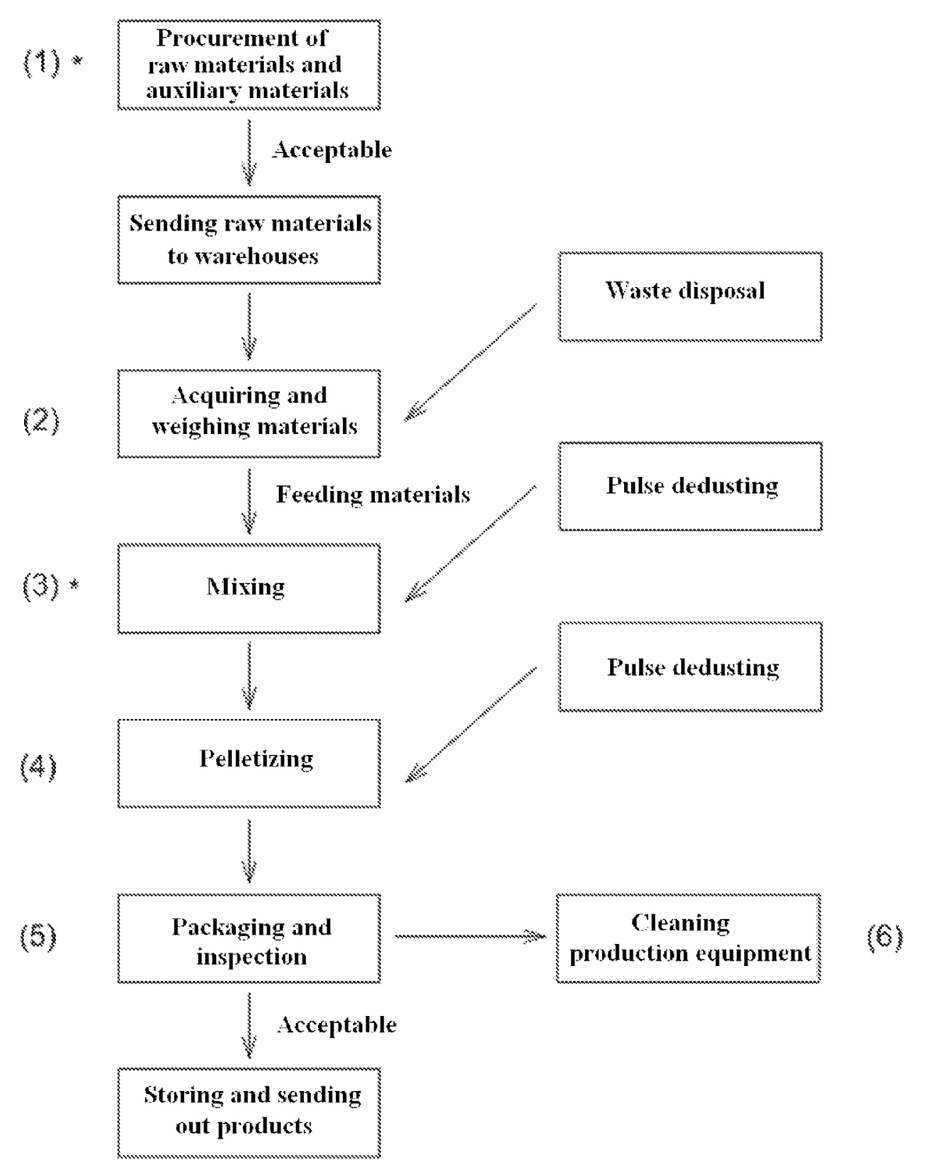
The FIGURE is a flow chart for the preparation of a hybrid pellet feed additive, wherein * represents a key control point.

In order to make the objectives, technical solutions, and advantages of the present invention clearer, the compounds, compositions, and applications of the present invention are further described in detail through the following embodiments. It should be understood that the specific embodiments described herein are only used to explain the present invention but are not intended to limit the present invention.

I. Preparation of Polyvalent Metal Ion Compound Salts of N,N-Dimethylglycine and Organic Acid Embodiment 1

Calcium salt of N,N-dimethylglycine and benzoic acid, having the following chemical formula:

28.00 g (200.60 mmol, 1.00 eq) of N,N-dimethylglycine hydrochloride (referred to as DMG hydrochloride) and 350 mL of absolute ethanol were successively added into a 1 L three-neck flask with vigorous stirring at room temperature to give a uniform suspension. 8.2 g of solid sodium hydroxide was added into the reaction system in batches (1 g×8, 205.0 mmol, 1.02 eq) with heat releasing, and the reaction system was stirred at room temperature for 0.5 hour. 25.0 g (204.7 mmol, 1.02 eq) of acicular crystalline solid benzoic acid was added with vigorous stirring at room temperature to give a uniform dispersion. 15.0 g (202.45 mmol, 1.01 eq) of powdery calcium hydroxide was added and the resulting mixture was stirred for 1 hour to give a white viscous reaction mixture. 80 mL of absolute ethanol was added into the reaction system, which was then stirred vigorously for 3 hours to give a white suspension. The white suspension was subjected to suction filtration, and the cake was washed with absolute ethanol (50 mL×3) and dried under reduced pressure at 110° C. overnight to give the product as off-white powders. The yield was 35.4 g (67.1%). $^1$HNMR (400 MHz, D$_2$O): δ(ppm) 2.13 (s, 6H), 2.82 (s, 2H), 7.27-7.39 (m, 3H), 8.01-8.03 (m, 2H).

Embodiment 2

Calcium salt of N,N-dimethylglycine and sulfuric acid, having the following chemical formula:

28.00 g (200.60 mmol, 1.00 eq) of N,N-dimethylglycine hydrochloride and 300 mL of absolute ethanol were successively added into a 1 L three-neck flask with vigorous stirring at room temperature to give a uniform suspension. 8.2 g of solid sodium hydroxide was added into the reaction system in batches (1 g×8, 205.0 mmol, 1.02 eq) with heat releasing, and the reaction system was stirred at room temperature for 0.5 hour. The reaction solution was cooled to −20° C. 9.84 g (100.30 mmol, 0.50 eq) of concentrated sulfuric acid was added dropwise into the reaction mixture with vigorous stirring. After the temperature of the reaction solution rose to room temperature, 15.0 g (202.45 mmol, 1.01 eq) of powdery calcium hydroxide was added and the resulting mixture was stirred for 1 hour to give a milky viscous reaction mixture. Absolute ethanol 80 mL was added into the reaction system, which was then stirred vigorously for 3 hours to give a white suspension. The white suspension was subjected to suction filtration, and the cake was washed with absolute ethanol (50 mL×3) and dried under reduced pressure at 110° C. overnight to give the product as white powders. The yield was 23.36 g (83.671%).

Embodiment 3

Calcium salt of N,N-dimethylglycine and phosphoric acid, having the following chemical formula:

28.00 g (200.60 mmol, 1.00 eq) of DMG hydrochloride was added into 300 mL of absolute ethanol, then 8.02 g (200.60 mmol, 1.00 eq) of solid NaOH was added under vigorous stirring with severe heat releasing. 7.86 g (68.20 mmol, 0.34 eq) of 85% phosphoric acid was added dropwise, followed by the addition of 15.00 g (202.45 mmol, 1.00 eq) of solid Ca(OH)$_2$, and then the reaction solution was stirred at room temperature for 1 hour to give a milky solution. 100 mL of absolute ethanol was added to the milky solution. The resulting reaction mixture was stirred for 3 hours and then subjected to suction filtration to give filter cake as white solid. The cake was washed with absolute ethanol (50 mL×3) and dried under reduced pressure at 50° C. overnight to give the product as white solid. The yield was 27.58 g (77.53%).

Embodiment 4

Calcium salt of N,N-dimethylglycine and fumaric acid, having the following chemical formula:

28.00 g (200.60 mmol, 1.00 eq) of DMG hydrochloride was added into 300 mL of absolute ethanol, then 8.02 g (200.60 mmol, 1.00 eq) of solid NaOH was added with vigorous stirring and severe heat releasing. 11.64 g (100.30 mmol, 0.50 eq) of fumaric acid and 15.00 g (202.45 mmol, 1.00 eq) of solid Ca(OH)$_2$ were successively added at room temperature into the reaction mixture, which was then stirred at room temperature for 1 hour to give a milky solution. 100 mL of absolute ethanol was added to the milky solution. The resulting mixture was stirred for 3 hours and then subjected to suction filtration to give filter cake as white solid. The filter cake was washed with absolute ethanol (50 mL×3) and dried under reduced pressure at 50° C. overnight to give the product as white solid. The yield was 27.66 g (69.21%).
$^1$HNMR (400 MHz, DMSO-d6): δ (ppm) 2.22 (s, 6H), 2.97 (s, 2H), 6.50 (s, 2H).

Embodiment 5

Calcium salt of N,N-dimethylglycine and tetradecanoic acid, having the following chemical formula:

28.00 g (200.60 mmol, 1.00 eq) of DMG hydrochloride was added into 300 mL of absolute ethanol, then 8 g (200.01 mmol, 1.00 eq) of solid NaOH was added with vigorous stirring and severe heat releasing. At room temperature, the solution was further stirred for 0.5 hour and then 45.81 g (200.60 mmol, 1.00 eq) of tetradecanoic acid and 15.00 g (202.45 mmol, 1.01 eq) of solid Ca(OH)$_2$ were successively added into the reaction solution. The resulting reaction mixture was then stirred at room temperature for 1 hour to give a milky solution. 100 mL of absolute ethanol was added to the milky solution and the resulting reaction mixture was stirred for 3 hours and then subjected to suction filtration to give filter cake as white solid. The filter cake was washed with absolute ethanol (100 mL×3) and dried under reduced pressure at 50° C. overnight to give the product as white solid. The yield was 62.52 g (84.33%).

Embodiment 6

Calcium salt of N,N-dimethylglycine and p-methylbenzenesulfonic acid, having the following chemical formula:

28.00 g (200.60 mmol, 1.00 eq) of DMG hydrochloride was added into 300 mL of absolute ethanol, then 8 g (200.01 mmol, 1.00 eq) of solid NaOH was added with vigorous stirring and severe heat releasing. At room temperature, the solution was further stirred for 0.5 hour and then 34.50 g (200.35 mmol, 1.00 eq) of p-methylbenzenesulfonic acid and 15.00 g (202.45 mmol, 1.01 eq) of solid Ca(OH)$_2$ were successively added into the reaction solution. The resulting reaction mixture was then stirred at room temperature for 1 hour to give a milky solution. 100 mL of absolute ethanol was added to the milky solution. The resulting reaction mixture was stirred for 3 hours and then subjected to suction filtration to give filter cake as white solid. The filter cake was washed with absolute ethanol (50 mL×3) and dried under reduced pressure at 50° C. overnight to give the product as white solid. The yield was 46.66 g (74.23%).

Embodiment 7

Copper salt of N,N-dimethylglycine and benzoic acid, having the following chemical formula:

28.00 g (200.60 mmol, 1.00 eq) of N,N-dimethylglycine hydrochloride (referred to as DMG hydrochloride) and 350 mL of absolute ethanol were successively added into a 1 L three-neck flask with vigorous stirring at room temperature to form a uniform suspension. 8.03 g of solid sodium hydroxide was added in batches (1 g×8, 200.76 mmol, 1.00 eq) into the reaction system with heat releasing and then the resulting reaction mixture was stirred at room temperature for 0.5 hour. To the reaction system was added with 24.50 g (200.60 mmol, 1.00 eq) of acicular crystalline solid benzoic acid with vigorous stirring at room temperature to give uniform dispersion in the reaction solution. 19.57 g (200.60 mmol, 1.00 eq) of powdery copper hydroxide was added into the reaction system and the resulting reaction mixture was stirred for 1 hour to give a light-blue viscous reaction solution. 80 mL of absolute ethanol was added into the reaction system, which was then stirred vigorously for 3 hours to give a light-blue suspension. The suspension was subjected to suction filtration, and the filter cake was washed with absolute ethanol (50 mL×3) and dried under reduced pressure at 110° C. overnight to give the product as white sand-like powders. The yield was 34.14 g (59.34%).

Embodiment 8

Zinc salt of N,N-dimethylglycine and benzoic acid, having the following chemical formula:

28.00 g (200.60 mmol, 1.00 eq) of N,N-dimethylglycine hydrochloride (referred to as DMG hydrochloride) and 350 mL of absolute ethanol were successively added into a reactor with vigorous stirring at room temperature to form a uniform suspension. 8.03 g of solid sodium hydroxide was added in batches (1 g×8, 200.76 mmol, 1.00 eq) into the reaction system with heat releasing, and then the system was stirred at room temperature for 0.5 hour. To the reaction system was then added with 24.50 g (200.60 mmol, 1.00 eq) of acicular crystalline solid benzoic acid with vigorous stirring at room temperature to give the reaction solution as uniform dispersion. 19.57 g (200.60 mmol, 1.00 eq) of powdery zinc hydroxide was added into the reaction system and the resulting reaction mixture was stirred for 1 hour to give a white viscous reaction solution. 80 mL of absolute ethanol was added into the reaction system, and the mixture was then stirred vigorously for 3 hours to give a white suspension. The suspension was subjected to suction filtration. The filter cake was washed with absolute ethanol (50 mL×3) and dried under reduced pressure at 110° C. overnight to give the product as white sand-like powders. The yield was 31.06 g (53.65%).

Embodiment 9

Zinc salt of N,N-dimethylglycine and fumaric acid, having the following chemical formula:

28.00 g (200.60 mmol, 1.00 eq) of DMG hydrochloride was added into 300 mL of absolute ethanol, then 8.02 g (200.60 mmol, 1.00 eq) of solid NaOH was added under vigorous stirring with severe heat releasing. 11.64 g (100.30 mmol, 0.50 eq) of fumaric acid and 20.00 g (201.22 mmol, 1.00 eq) of solid $Zn(OH)_2$ were successively added at room temperature into the reaction solution, which was then stirred at room temperature for 1 hour to give a milky solution. 100 mL of absolute ethanol was added to the milky solution and the resulting reaction mixture was stirred for 3 hours. The reaction solution was then subjected to suction filtration to give filter cake as white solid. The filter cake was washed with absolute ethanol (50 mL×3) and dried under reduced pressure at 50° C. overnight to give the product as white solid. The yield was 24.16 g (53.65%).

Embodiment 10

Copper salt of N,N-dimethylglycine and fumaric acid, having the following chemical formula:

28.00 g (200.60 mmol, 1.00 eq) of DMG hydrochloride was added into 300 mL of absolute ethanol, then 8.02 g (200.60 mmol, 1.00 eq) of solid NaOH was added under vigorous stirring with severe heat releasing. 11.64 g (100.30 mmol, 0.50 eq) of fumaric acid and 19.60 g (200.60 mmol, 1.00 eq) of solid $Cu(OH)_2$ were successively added at room temperature into the reaction solution, and the resulting reaction mixture was then stirred at room temperature for 1 hour to give a milky solution. 100 mL of absolute ethanol was added to the milky solution. The resulting mixture was stirred for 3 hours and then subjected to suction filtration to give filter cake as white solid. The filter cake was washed with absolute ethanol (50 mL×3) and dried under reduced pressure at 50° C. overnight to give the product as white solid. and the yield was 32.64 g (73.06%).

II. Related Properties of Polyvalent Metal Ion Compound Salts of N,N-Dimethylglycine and Organic Acid Test samples and suppliers are as follows:
Sample 1: N,N-dimethylglycine hydrochloride, from J&K Scientific Ltd.
Sample 2: Sodium N,N-dimethylglycinate, from Shandong Xiya Chemical Industry Co., Ltd.
Sample 3: Calcium N,N-dimethylglycinate, from R&D center of Guangzhou Insighter Biotechnology Co., Ltd.
Sample 4: Calcium benzoate, from R&D center of Guangzhou Insighter Biotechnology Co., Ltd.
Sample 5: Calcium salt of N,N-dimethylglycine and benzoic acid, prepared in Embodiment 1.
Sample 6: Calcium salt of N,N-dimethylglycine and sulfuric acid, prepared in Embodiment 2.
Sample 7: Calcium salt of N,N-dimethylglycine and phosphoric acid, prepared in Embodiment 3.
Sample 8: Calcium salt of N,N-dimethylglycine and fumaric acid, prepared in Embodiment 4.
Sample 9: Calcium salt of N,N-dimethylglycine and tetradecanoic acid, prepared in Embodiment 5.
Sample 10: Calcium salt of N,N-dimethylglycine and p-methylbenzenesulfonic acid, prepared in Embodiment 6.
Sample 11: Copper salt of N,N-dimethylglycine and benzoic acid, prepared in Embodiment 7.
Sample 12: Zinc salt of N,N-dimethylglycine and benzoic acid, prepared in Embodiment 8.
Sample 13: Zinc salt of N,N-dimethylglycine and fumaric acid, prepared in Embodiment 9.

Sample 14: Copper salt of N,N-dimethylglycine and fumaric acid, prepared in Embodiment 10.

1. Appearance and Melting Point Determination

TABLE 1

Appearance and melting point determination of polyvalent metal ion compound salts of N,N-dimethylglycine and organic acid

| Test sample | Appearance | Melting point/° C. |
|---|---|---|
| N,N-dimethylglycine hydrochloride | White crystalline particles | 189-193 |
| Sodium N,N-dimethylglycinate | White powders | 217° C. |
| Calcium N,N-dimethylglycinate | White powders | 220° C., not melted, decomposed |
| Calcium benzoate | White powders | >260° C., not melted, not decomposed |
| Sample 5 | White powders | >24° C. not melted, decomposed |

2. High-Humidity Stability Test

Method: A $KNO_3$ saturated solution (25° C., RH 90%) was placed in the lower part of a constant-temperature and constant-humidity sealed container. The test samples, three parallels for each test sample, were placed at 25° C. and RH 95%±1% for 10 days, and their average weight gains were measured at day 5 and day 10.

Results: The test data was statistically analyzed using SPSS18 software. The test results are expressed as "mean value±standard error" as shown in Table 2. At 25° C. and RH 95%, the sample 1, sample 2, and sample 3, which were respectively hydrochloride, sodium salt and calcium salt of DMG, showed very high hygroscopicity, the weight gains of the test samples at day 5 turn the samples into water-like status. Sample 6 and sample 7 were respectively calcium salt of N,N-dimethylglycine and sulfuric acid and calcium salt of N,N-dimethylglycine and phosphoric acid, their hygroscopic weight gains reached 60%-65% at day 5, and the samples were water-like status. Sample 5 and samples 8-14 were respectively calcium salt of N,N-dimethylglycine and organic acid, copper salt of N,N-dimethylglycine and organic acid or zinc salt of N,N-dimethylglycine and organic acid, showing a hygroscopic weight gain of no higher than 3.6% at day 5, and no significant difference in hygroscopic weight gain were observed between day 5 and day 10.

Conclusion: After placed for 10 days under a constant-temperature and constant-humidity condition of 25° C. and RH 95%±1%, all the polyvalent metal ion compound salts of N,N-dimethylglycine and organic acid showed a hygroscopic weight gain of lower than 5% and relative stability, satisfying the requirements of feed additives on humidity.

TABLE 2

High-humidity stability study of polyvalent metal ion compound salts of N,N-dimethylglycine and organic acid

| Compound | Day 5 (%) | Day 10 (%) |
|---|---|---|
| Sample 1 | 79.86 ± 0.94 | 80.69 ± 0.59 |
| Sample 2 | 49.09 ± 1.14 | 52.44 ± 0.48 |
| Sample 3 | 38.40 ± 0.22 | 41.83 ± 0.35 |
| Sample 5 | 3.54 ± 0.39 | 3.59 ± 0.28 |
| Sample 6 | 61.72 ± 0.41 | 60.58 ± 0.21 |
| Sample 7 | 63.86 ± 0.17 | 64.83 ± 0.23 |
| Sample 8 | 2.95 ± 0.22 | 3.25 ± 0.12 |
| Sample 9 | 2.11 ± 0.04 | 2.75 ± 0.32 |
| Sample 10 | 2.84 ± 0.23 | 3.01 ± 0.11 |
| Sample 11 | 2.41 ± 0.07 | 2.81 ± 0.10 |
| Sample 12 | 3.03 ± 0.23 | 3.54 ± 0.08 |
| Sample 13 | 2.26 ± 0.09 | 2.76 ± 0.23 |
| Sample 14 | 2.56 ± 0.11 | 2.81 ± 0.06 |

III. Preparation Method of Feed Composition

The polyvalent metal ion compound salts of N,N-dimethylglycine and organic acid from embodiment 1-10 were respectively mixed with a corresponding auxiliary material to prepare a corresponding hybrid pellet feed additive.

1. Materials

Raw materials: The polyvalent metal ion compound salts of N,N-dimethylglycine and organic acid from embodiment 1-10, and sodium N,N-dimethylglycinate.

Carrier: Corn starch.

Binder: 1.3% hydroxypropyl methyl cellulose aqueous solution.

2. Product Formula

TABLE 3

Formula of hybrid pellet feed additives of polyvalent metal ion compound salts of N,N-dimethylglycine and organic acid

| Product name | Raw material/parts by mass | Carrier/ parts by mass | Binder/ parts by mass |
|---|---|---|---|
| Reference 1 | Sodium N,N-dimethylglycinate 20 | 80 | 35 |
| Product 1 | Calcium salt of N,N-dimethylglycine and benzoic acid 20 | 80 | 35 |
| Product 2 | Calcium salt of N,N-dimethylglycine and fumaric acid 20 | 80 | 35 |
| Product 3 | Calcium salt of N,N-dimethylglycine and tetradecanoic acid 20 | 80 | 35 |
| Product 4 | Calcium salt of N,N-dimethylglycine and p-methylbenzenesulfonic acid 20 | 80 | 35 |
| Product 5 | Copper salt of N,N-dimethylglycine and benzoic acid 20 | 80 | 35 |
| Product 6 | Zinc salt of N,N-dimethylglycine and benzoic acid 20 | 80 | 35 |
| Product 7 | Zinc salt of N,N-dimethylglycine and fumaric acid 20 | 80 | 35 |
| Product 8 | Copper salt of N,N-dimethylglycine and fumaric acid 20 | 80 | 35 |

3. Production Process

Production process of the hybrid pellet feed additive involved in the present invention is described below in combination with The FIGURE.

Raw material supply: The raw materials were supplied by the R&D center of Guangzhou Insighter Biotechnology Co., Ltd., and inspected by the quality control department as acceptable products with a purity of ≥99%.

Procurement of auxiliary materials: The auxiliary materials were purchased from qualified suppliers. After determined to be acceptable by sampling inspection, the auxiliary materials were sent to warehouses and stored for later use. This step is a key control point that quality of the auxiliary materials must be strictly controlled.

Acquiring and weighing materials: The raw materials and the auxiliary materials were successively weighed and double-checked according to the proportions in the formulas, while the produced wastes (bags) were stored and disposed together.

Mixing: The raw materials and the auxiliary materials were fed into a mixer to mix well. This step is a key control point that the mixing time must be strictly controlled by regular inspection of mixing uniformity. The mixer was equipped with a pulse dust collector to remove dust.

Pelletizing: The products obtained from mixing the raw materials and the auxiliary materials were introduced into a pelletizing machine with a 1.3% hydroxypropyl methyl cellulose aqueous solution according to a mass ratio of 100:35. The pelletizing machine was then started up to operate mixing and cutter for 3-5 minutes. After pelletizing was complete, the materials were dried in a fluidized bed for 30 minutes and then sieved by 16-mesh sieve.

Packaging and inspection: The products were weighed and packaged according to packaging specifications, stored in finished-product warehouses, and labeled with production and inspection information. At least two samples were collected for each batch and sent to the testing laboratory for inspection and as reserve samples. The products would be allowed to leave the factory only after passing the inspection. Thereby the hybrid pellet feed additive was obtained.

Cleaning production equipment: After production of each batch was complete, the production area must be cleaned. When changing the product, the production equipment shall be cleaned to remove impurities in order to prevent cross-contamination.

III. Animal Breeding Experiment

Embodiment A: Application Effect of Polyvalent Metal Ion Compound Salts of N,N-Dimethylglycine and Organic Acid in Broiler Feed The test was carried out by single-factor randomized design. 1200 22-day-old Sanhuang broilers having similar body weight (averagely 153 g) were collected and randomly divided into 10 groups, 6 replicates in each group, 20 broilers in each replicate, with equal numbers of males and females. The henhouse and utensils were disinfected before the test. The broilers were kept in cages in the same henhouse under the same breeding conditions during the experiment. The basic diets mainly composed of corn and soybean meal, and no other antioxidant ingredients and growth promoters were added during the whole breeding process. The groups included a blank group, a control group, and test groups 1-8. The blank group was provided with only the basal ration, while the control group and the test groups 1-8 were respectively provided with 5000 ppm of the hybrid pellet feed additive products (see the "Preparation method of feed composition" section) in the basic diets. The experiment was carried out for 20 days, wherein the experiment broilers were fed with food and water ad libitum, and the diets were provided twice a day. For each replicate, the broilers were weighed (stopped feeding for 12 hours while water supply was maintained) at 42-day-old and their feed consumptions were recorded so as to calculate the average daily feed intake (ADFI), average daily weight gain (ADG) and feed conversion ratio (FCR). The experiment data were analyzed with SPSS18 software. The data were first analyzed by single factor analysis of variance (ANOVA), and if the differences between the groups were significant, multiple comparisons were performed using Duncan's method wherein the significance level was 0.05. Test results are expressed as "mean value±standard error" as shown in Table 4. As can be seen from the results, compared with the blank group, the sample of control group showed a significant improvement effect on the feed intake, average daily weight gain and feed conversion ratio of the experiment broilers. Compared with the blank group, the samples of experiment groups 1-8 showed no significant effect on the feed intake of the test broilers, but a significant increase in the average daily weight gains and a significant reduction in the feed conversion ratio. By comparing the experiment groups 1-8 with the control group, the experiment groups 1-4 showed no significant improvement in the feed conversion ratio while the test groups 6-8 showed significant reduction in the feed conversion ratio.

Conclusion: In the breeding experiment of broilers, with respect to feed conversion efficiency, the calcium salt of N,N-dimethylglycine and benzoic acid, calcium salt of N,N-dimethylglycine and fumaric acid, calcium salt of N,N-dimethylglycine and tetradecanoic acid and calcium salt of N,N-dimethylglycine and p-methylbenzenesulfonic acid provided by the present invention showed a breeding effect equivalent to that of sodium N,N-dimethylglycinate, while the copper salt of N,N-dimethylglycine and benzoic acid, zinc salt of N,N-dimethylglycine and benzoic acid, copper salt of N,N-dimethylglycine and fumaric acid and zinc salt of N,N-dimethylglycine and fumaric acid provided by the present invention showed a breeding effect higher than that of N,N-dimethylglycine hydrochloride, giving a 11% reduction in the feed conversion ratio as compared with the group which was not provided with any feed additives.

TABLE 4

Effect of polyvalent metal ion compound salts of N,N-dimethylglycine and organic acid on the production performance of broilers

| | Sample | Amount | ADFI (g) | ADG (g) | FCR |
|---|---|---|---|---|---|
| Blank | — | 20*6 | 651.33 ± 15.00$^a$ | 216.00 ± 4.33$^a$ | 3.02 ± 0.02$^a$ |
| Control | Reference 1 | 20*6 | 703.00 ± 15.92$^b$ | 246.16 ± 8.30$^b$ | 2.86 ± 0.04$^d$ |
| Experiment 1 | Product 1 | 20*6 | 679.33 ± 15.80 | 246.07 ± 7.84$^b$ | 2.76 ± 0.03$^{cd}$ |
| Experiment 2 | Product 2 | 20*6 | 680.83 ± 12.64 | 247.08 ± 2.23$^b$ | 2.76 ± 0.04$^{cd}$ |
| Experiment 3 | Product 3 | 20*6 | 674.83 ± 13.29 | 237.29 ± 7.73$^b$ | 2.85 ± 0.04$^d$ |
| Experiment 4 | Product 4 | 20*6 | 681.83 ± 14.24 | 246.80 ± 7.98$^b$ | 2.77 ± 0.04$^{cd}$ |
| Experiment 5 | Product 5 | 20*6 | 664.00 ± 14.42 | 250.55 ± 8.81$^b$ | 2.66 ± 0.04$^b$ |
| Experiment 6 | Product 6 | 20*6 | 655.00 ± 12.25 | 247.59 ± 2.50$^b$ | 2.64 ± 0.04$^b$ |
| Experiment 7 | Product 7 | 20*6 | 660.50 ± 12.08 | 244.39 ± 1.80$^b$ | 2.70 ± 0.03$^{bc}$ |
| Experiment 8 | Product 8 | 20*6 | 679.33 ± 6.19 | 250.91 ± 4.53$^b$ | 2.71 ± 0.03$^{bc}$ |

Note:
Throughout the description hereinafter, data listed in the same column but labelled with different letters indicates there is a significant difference therebetween (P < 0.05); this rule is also applied hereinafter.

Embodiment B: Application Effect of Polyvalent Metal Ion Compound Salts of N,N-Dimethylglycine and Organic Acid in Pig Feed Two hundred and seventy (270) 65-day-old Duroc×Landrace×Large White pig having similar body weight were randomly divided into 9 groups, 3 replicates in each group, 10 pigs in each replicate, with equal numbers of males and females. The pigsty and utensils were disinfected before the experiment. The pigs were kept in pens in the same pigsty under the same breeding conditions during the experiment. During the experiment, the experiment pigs were fed with food and water ad libitum, and the ration were provided twice a day. The groups included a control group and experiment groups 1-8. The control group was provided with only the basic diets, while the experiment groups 1-8 were respectively provided with the basal ration together with 1150 ppm of the hybrid pellet feed additive products 1-8 provided by the present invention. No other antioxidant ingredients and growth promoters were added during the whole breeding process. The experiment was carried out for 28 days. For each replicate, production performance of the pigs was measured, including the average daily feed intake (ADFI), average daily weight gain (ADG) and feed conversion ratio (FCR). The experiment data were analyzed with SPSS18 software. The data were first analyzed by single factor analysis of variance (ANOVA), and if the differences between the groups were significant, multiple comparisons were performed using Duncan's method wherein the significance level was 0.05. Test results are expressed as "mean value±standard error" as shown in Table 5. As can be seen from the results, compared with the control group, the experiment groups, which were provided with the polyvalent metal ion compound salts of N,N-dimethylglycine and organic acid, showed no significant effect on the feed intake of the pigs but a significant increase in the average daily weight gains and a reduction of 7.0%-12.5% in the feed conversion ratio.

TABLE 5

Effect of polyvalent metal ion compound salts of N,N-dimethylglycine and organic acid on the production performance of pigs

| | Sample | Amount | ADFI (kg) | ADG (kg) | FCR |
|---|---|---|---|---|---|
| Control | | 10*3 | 11.87 ± 0.32 | 4.51 ± 0.08$^a$ | 2.63 ± 0.02$^a$ |
| Experiment 1 | Product 1 | 10*3 | 12.73 ± 0.33 | 5.26 ± 0.10$^b$ | 2.42 ± 0.02$^b$ |
| Experiment 2 | Product 2 | 10*3 | 12.40 ± 0.26 | 5.13 ± 0.07$^b$ | 2.42 ± 0.02$^b$ |
| Experiment 3 | Product 3 | 10*3 | 12.77 ± 0.20 | 5.22 ± 0.10$^b$ | 2.44 ± 0.01$^b$ |
| Experiment 4 | Product 4 | 10*3 | 12.53 ± 0.32 | 5.17 ± 0.14$^b$ | 2.43 ± 0.01$^b$ |
| Experiment 5 | Product 5 | 10*3 | 12.53 ± 0.27 | 5.44 ± 0.12$^b$ | 2.30 ± 0.01$^e$ |
| Experiment 6 | Product 6 | 10*3 | 12.43 ± 0.43 | 5.27 ± 0.21$^b$ | 2.37 ± 0.01$^c$ |
| Experiment 7 | Product 7 | 10*3 | 12.50 ± 0.38 | 5.31 ± 0.18$^b$ | 2.36 ± 0.01$^{cd}$ |
| Experiment 8 | Product 8 | 10*3 | 12.70 ± 0.26 | 5.49 ± 0.13$^b$ | 2.31 ± 0.01$^{de}$ |

Embodiment C: Application Effect of Polyvalent Metal Ion Compound Salts of N,N-Dimethylglycine and Organic Acid in Aquatic Feed (1) Experiment Materials Test fish: The experiment fish were grass carps, born at the year of the test, from Dafeng hatchery in Huizhou City, Guangdong Province. Healthy and lively grass carps of the same size were reared in big net cages (4×2×1.5 m³) for four weeks before the breeding test. The test system included floating small net cages (1.1×1.1×1.1 m³), each small net cage was provided with an aerator and aerated 24 hours every day. The small net cages were disposed together with temporary-rearing net cages in a 3500 m² pond in the test area, the pond had a depth of 1.55 m and the water in the pond was fully aerated groundwater. 432 fish which had been starved for 1 day were randomly divided into 9 groups, 4 replicates in each group and 12 fish in each replicate. The fish of each replicate were weighed and transferred to 36 net cages, and fed with different test feeds respectively.

Test feeds: The test feeds were prepared according to Table 6. The groups were respectively provided with different polyvalent metal ion compound salts of N,N-dimethylglycine and organic acid in the same concentration according to Table 7. Raw materials of the feed were ultra-pulverized, and then turned into floating expanded feed having a particle size of 3 mm by using a feed extruder from Jiangsu Muyang Group Co., Ltd. wherein the extruding temperature was 130° C., and 3% of soybean oil was sprayed on the feed using an oil sprayer. The feed was then sealed and stored in a cool place for later use.

TABLE 6

Formula and chemical composition of the test feed for grass carp (% wt.)

| Raw material | Content (%) | Raw material | Content (%) |
|---|---|---|---|
| Fish meal | 9.0 | Soybean oil | 3.0 |
| Intestine submucosa powder | 3.0 | Phospholipid rapeseed meal | 9.0 |
| Soybean meal | 12.0 | Gluten flour | 4.0 |
| Rapeseed meal | 12.0 | Blood cell powder | 2.0 |
| MSG protin | 3.0 | Vc-phosphate ester | 0.1 |
| Wheat middling | 12.6 | Monocalcium phosphate | 1.8 |
| Flour | 17.0 | Choline chloride | 0.2 |
| Bentonite | 0.70 | Multi-vitamin | 0.1 |
| Rice bran | 10.0 | Trace mineral element premix | 0.5 |

TABLE 7

Grouping of growth promotion test of polyvalent metal ion compound salts of N,N-dimethylglycine and organic acid

| Group | Sample | Concentration (ppm) |
|---|---|---|
| Blank control | — | — |
| Experiment 1 | Calcium salt of N,N-dimethylglycine and benzoic acid | 450 |
| Experiment 2 | Calcium salt of N,N-dimethylglycine and fumaric acid | 450 |

TABLE 7-continued

Grouping of growth promotion test of polyvalent metal ion
compound salts of N,N-dimethylglycine and organic acid

| Group | Sample | Concentration (ppm) |
|---|---|---|
| Experiment 3 | Calcium salt of N,N-dimethylglycine and tetradecanoic acid | 450 |
| Experiment 4 | Calcium salt of N,N-dimethylglycine and p-methylbenzenesulfonic acid | 450 |

(3) Experiment Results

Effect of polyvalent metal ion compound salts of N,N-dimethylglycine and organic acid on the production performance of grass carps is as shown in Table 8. Results showed that, the groups provided with polyvalent metal ion compound salts of N,N-dimethylglycine and organic acid were better than the blank control group in terms of weight gain and feed conversion ratio, indicating obvious growth-promotion effects, and the survival rate of grass carps were also significantly improved, indicating an significant improvement of anoxic resistance of grass carps.

TABLE 8

Test results of application of polyvalent metal ion compound
salts of N,N-dimethylglycine and organic acid in aquatic feed

|  | Initial weight (g) | Final weight (g) | Weight gain (%) | (FCR) | SR (%) |
|---|---|---|---|---|---|
| Blank control | 251.25 ± 4.09 | 585.55 ± 11.53 | 133.15 ± 4.54 | 1.50 ± 0.05 | 56.25 ± 9.24$^a$ |
| Experiment 1 | 253.25 ± 4.19 | 596.47 ± 13.08 | 135.48 ± 2.16 | 1.46 ± 0.04 | 85.42 ± 3.99$^b$ |
| Experiment 2 | 254.25 ± 3.64 | 598.31 ± 5.61 | 135.48 ± 4.28 | 1.46 ± 0.06 | 89.58 ± 3.99$^b$ |
| Experiment 3 | 250.50 ± 3.38 | 598.90 ± 9.16 | 139.15 ± 3.65 | 1.44 ± 0.03 | 75.00 ± 7.61$^b$ |
| Experiment 4 | 252.50 ± 2.84 | 602.98 ± 4.17 | 138.90 ± 3.17 | 1.43 ± 0.02 | 81.25 ± 7.11$^b$ |
| Experiment 5 | 256.25 ± 2.01 | 608.72 ± 5.87 | 137.60 ± 3.16 | 1.42 ± 0.03 | 79.17 ± 5.38$^b$ |
| Experiment 6 | 253.00 ± 1.78 | 604.66 ± 10.81 | 138.96 ± 3.28 | 1.43 ± 0.04 | 79.16 ± 8.67$^b$ |
| Experiment 7 | 253.25 ± 2.29 | 607.01 ± 6.05 | 139.76 ± 3.47 | 1.42 ± 0.03 | 93.75 ± 3.99$^b$ |
| Experiment 8 | 255.25 ± 1.31 | 608.50 ± 9.48 | 138.44 ± 4.43 | 1.42 ± 0.04 | 95.83 ± 2.40$^b$ |

TABLE 7-continued

Grouping of growth promotion test of polyvalent metal ion
compound salts of N,N-dimethylglycine and organic acid

| Group | Sample | Concentration (ppm) |
|---|---|---|
| Experiment 5 | Copper salt of N,N-dimethylglycine and benzoic acid | 450 |
| Experiment 6 | Zinc salt of N,N-dimethylglycine and benzoic acid | 450 |
| Experiment 7 | Zinc salt of N,N-dimethylglycine and fumaric acid | 450 |
| Experiment 8 | Copper salt of N,N-dimethylglycine and fumaric acid | 450 |

(2) Experiment Method

Test management: The test was carried out with ration restriction, the ration amount was adjusted once a week, the feeding level (based on initial weight) of each group was exactly the same, and feeding was conducted twice every day (at 7:30 and 15:00). The test was carried out for 8 weeks. During the experiment, water quality was monitored regularly to maintain the following conditions: water temperature 26.88±3.08° C., DO>5.0 mg O L$^{-1}$, pH 7.8, ammonia nitrogen<0.50 mg N L$^{-1}$, and nitrite nitrogen<0.05 mg N L$^{-1}$.

Parameter statistics: In the experiment, the fish in each net cage were weighed as a whole after starved for 1 day so as to calculate their weight gain (WG, %), feed conversion ratio (FCR) and survival rate (SR, %), through the following formula.

Weight gain (WG,%)=100×(average final weight−average initial weight)/average initial weight Feed conversion ratio (FCR)=feed intake/fish weight gain Survival rate (SR,%)=100×fish amount at the end of the test/fish amount at the beginning of the test Embodiment D: Study on Application of Zinc Salt of N,N-Dimethylglycine and Fumaric Acid in Weaned-Pig Feed Two hundred and forty (240) lean Duroc×Landrace× Large White weaned pigs having similar body weight were randomly divided into 8 groups, 3 replicates in each group, 10 pigs in each replicate, with equal numbers of males and females. The pigsty and utensils were disinfected before the experiment. The pigs were kept in pens in the same pigsty under the same breeding conditions during the experiment. During the experiment, the experiment pigs were fed with food and water ad libitum, and the diets were provided 3 times a day. The groups included a control group, a comparative example and experiment groups 1-6. The control group was provided with only the basic diets, the comparative example was provided with 2500 ppm of zinc oxide, and the experiment groups 1-6 were respectively provided with the basic diets together with the hybrid pellet feed additive product 7 provided by the present invention in different concentrations, as shown in Table 9. No other antioxidant ingredients and growth promoters were added during the whole breeding process. The experiment was carried out for 15 days. For each replicate, production performance of the pigs was measured, including the average daily feed intake (ADFI), average daily weight gain (ADG) and feed conversion ratio (FCR). The experiment data were analyzed with SPSS18 software. The data were first analyzed by single factor analysis of variance (ANOVA), and if the differences between the groups were significant, multiple comparisons were performed using Duncan's method wherein the significance level was 0.05. Experiment results are expressed as "mean value±standard error" as shown in Table 9. As can be seen from the results, zinc salt of N,N-dimethylglycine and fumaric acid had no significant effect on the feed intake of weaned pigs; effect on the average daily weight gain was dose dependent, wherein about 260 ppm of the salt could significantly increase the average daily weight gain of weaned pigs to a level realized by 2500 ppm of zinc oxide; the salt could also reduce the feed conversion ratio, but the effect would only be significant and equivalent to that of high-dose zinc oxide when the dose was higher than 390 ppm.

TABLE 9

Effect of zinc salt of N,N-dimethylglycine and fumaric acid on production performance of weaned pigs

| | Sample | Dose/ppm | ADFI (kg) | ADG (kg) | FCR |
|---|---|---|---|---|---|
| Control | — | — | 82.50 ± 3.75 | 40.20 ± 1.23$^a$ | 2.050 ± 0.033 |
| Comparative example | Zinc oxide | 2500 | 82.15 ± 2.31 | 45.43 ± 0.84$^b$ | 1.808 ± 0.018 |
| Experiment 1 | Product 7 | 55 | 81.73 ± 3.83 | 40.93 ± 1.18$^a$ | 2.005 ± 0.152 |
| Experiment 2 | Product 7 | 65 | 78.33 ± 1.19 | 41.40 ± 1.36$^a$ | 1.898 ± 0.091 |
| Experiment 3 | Product 7 | 130 | 80.65 ± 2.22 | 43.10 ± 1.27$^a$ | 1.878 ± 0.108 |
| Experiment 4 | Product 7 | 260 | 83.13 ± 3.47 | 45.50 ± 0.91$^b$ | 1.826 ± 0.040 |
| Experiment 5 | Product 7 | 390 | 84.59 ± 2.08 | 46.57 ± 1.70$^b$ | 1.818 ± 0.022 |
| Experiment 6 | Product 7 | 520 | 83.88 ± 3.20 | 47.36 ± 1.42$^b$ | 1.770 ± 0.187 |

Note:
The compound concentrations in the samples were calculated in terms of zinc element.

Embodiment E: Application Effect of Copper Salt of N,N-Dimethylglycine and Fumaric Acid on Weaned Pigs One hundred and eighty (180) lean Duroc×Landrace× Large White weaned pigs having similar body weight were randomly divided into 6 groups, 3 replicates in each group, 10 pigs in each replicate, with equal numbers of males and females. The pigsty and utensils were disinfected before the experiment. The pigs were kept in pens in the same pigsty under the same breeding conditions during the experiment. During the experiment, the experiment pigs were fed with food and water ad libitum, and the diets were provided 3 times a day. The groups included a control group, a comparative example and test groups 1-4. The control group was provided with only the basic diets, the comparative example was provided with 250 ppm of copper sulfate pentahydrate, and the experiment groups 1-4 were respectively provided with the basic diets together with the hybrid pellet feed additive product 8 provided by the present invention in different concentrations, as shown in Table 10. No other antioxidant ingredients and growth promoters were added during the whole breeding process. The test was carried out for 15 days. For each replicate, production performance of the pigs was measured, including the average daily feed intake (ADFI), average daily weight gain (ADG) and feed conversion ratio (FCR). The experiment data were analyzed with SPSS18 software. The data were first analyzed by single factor analysis of variance (ANOVA), and if the differences between the groups were significant, multiple comparisons were performed using Duncan's method wherein the significance level was 0.05. Test results are expressed as "mean value±standard error" as shown in Table 10. As can be seen from the results, copper salt of N,N-dimethylglycine and fumaric acid had no significant effect on the feed intake and average daily weight gain of weaned pigs, but could significantly reduce feed conversion ratio when the dose was 30-100 ppm; when the dose reached 100 ppm, the reduction of feed conversion ratio had reduced by 8.61% compared with the control group, similar to the effect of high-dose copper sulfate pentahydrate.

TABLE 10

Effect of N,N-dimethylglycine fumaric acid copper salt on production performance of weaned pigs

| | Sample | Dose/ppm | ADFI (kg) | ADG (kg) | FCR |
|---|---|---|---|---|---|
| Control | — | — | 93.67 ± 2.33 | 41.79 ± 1.03 | 2.241 ± 0.001$^a$ |
| Comparative example | Copper sulfate pentahydrate, | 250 | 94.67 ± 1.33 | 46.38 ± 1.01 | 2.042 ± 0.021$^b$ |
| Experiment 1 | Product 8 | 100 | 89.00 ± 1.73 | 43.46 ± 0.25 | 2.048 ± 0.028$^b$ |
| Experiment 2 | Product 8 | 75 | 90.00 ± 1.53 | 43.26 ± 1.35 | 2.083 ± 0.032$^{bc}$ |
| Experiment 3 | Product 8 | 50 | 94.00 ± 1.53 | 44.77 ± 1.28 | 2.101 ± 0.027$^{bc}$ |
| Experiment 4 | Product 8 | 30 | 94.67 ± 2.18 | 44.14 ± 1.39 | 2.146 ± 0.022$^c$ |

Note:
The compound concentrations in the samples were calculated in terms of copper element.

The above embodiments only illustrate several implementation manners of the present invention, and there are other manners for implementing the present invention. Accordingly, the embodiments of the present invention are described as examples, but they should not be construed as limiting the patent scope of the present invention, which may further include modifications made within the scope of the invention and within the same inventive concept or equivalents added to the claims.

What is claimed is:

1. A polyvalent metal ion compound salt of N,N-dimethylglycine and an organic acid, comprising an N,N-dimethylglycinate ion, a polyvalent metal ion in an amount equimolar to the N,N-dimethylglycinate ion, and an organic acid ion, wherein the organic acid ion is acceptable for a feed for an animal, and wherein the amount of the organic acid ion is such that the polyvalent metal ion compound salt that comprises the N,N-dimethylglycinate ion, the polyvalent metal ion and the organic acid ion exhibits an electron neutral status.

2. The polyvalent metal ion compound salt of N,N-dimethylglycine and the organic acid according to claim 1, characterized in that, the polyvalent metal ion is a divalent metal ion.

3. The polyvalent metal ion compound salt of N,N-dimethylglycine and the organic acid according to claim 2, characterized in that, the divalent metal ion is Ca(II), Mg(II), Cu(II), Zn(II), Fe(II), Mn(II), Co(II) or Ni(II).

4. The polyvalent metal ion compound salt of N,N-dimethylglycine and the organic acid according to claim 1, characterized in that, the organic acid is benzoic acid, p-toluic acid or fumaric acid.

5. The polyvalent metal ion compound salt of N,N-dimethylglycine and the organic acid according to claim 1, characterized in that, the polyvalent metal ion compound salt is selected from:
I. a polyvalent metal ion compound salt of N,N-dimethylglycine and the organic acid comprising the N,N-dimethylglycinate ion, Ca(II) ion in an amount equimolar to the N,N-dimethylglycinate ion, and benzoate ion, wherein the amount of the benzoate ion is such that the Ca(II) ion compound salt that comprises the N,N-dimethylglycinate ion, the Ca(II) ion and the benzoate ion exhibits an electron neutral status;
II. a polyvalent metal ion compound salt of N,N-dimethylglycine and the organic acid comprising the N,N-dimethylglycinate ion, Ca(II) ion in an amount equimolar to the N,N-dimethylglycinate ion, and fumarate ion, wherein the amount of the fumarate ion is such that the Ca(II) ion compound salt that comprises the N,N-dimethylglycinate ion, the Ca(II) ion and the fumarate ion exhibits an electron neutral status;
III. a polyvalent metal ion compound salt of N,N-dimethylglycine and the organic acid comprising the N,N-dimethylglycinate ion, Cu(II) ion in an amount equimolar to the N,N-dimethylglycinate ion, and benzoate ion, wherein the amount of the benzoate ion is such that the Cu(II) ion compound salt that comprises the N,N-dimethylglycinate ion, the Cu(II) ion and the benzoate ion exhibits an electron neutral status;
IV. a polyvalent metal ion compound salt of N,N-dimethylglycine and the organic acid comprising the N,N-dimethylglycinate ion, Cu(II) ion in an amount equimolar to the N,N-dimethylglycinate ion, and fumarate ion, wherein the amount of the fumarate ion is such that the Cu(II) ion compound salt that comprises the N,N-dimethylglycinate ion, the Cu(II) ion and the fumarate ion exhibits an electron neutral status;
V. a polyvalent metal ion compound salt of N,N-dimethylglycine and the organic acid comprising the N,N-dimethylglycinate ion, Zn(II) ion in an amount equimolar to the N,N-dimethylglycinate ion, and benzoate ion, wherein the amount of the benzoate ion is such that the Zn(II) ion compound salt that comprises the N,N-dimethylglycinate ion, the Zn(II) ion and the benzoate ion exhibits an electron neutral status; or
VI. a polyvalent metal ion compound salt of N,N-dimethylglycine and the organic acid comprising the N,N-dimethylglycinate ion, Zn(II) ion in an amount equimolar to the N,N-dimethylglycinate ion, and fumarate ion, wherein the amount of the fumarate ion is such that the Zn(II) ion compound salt that comprises the N,N-dimethylglycinate ion, the Zn(II) ion and the fumarate ion exhibits an electron neutral status.

6. A feed composition, comprising at least one of the polyvalent metal ion compound salt of N,N-dimethylglycine and the organic acid of claim 1 or a solvate thereof and an auxiliary material usable for feed.

7. The feed composition according to claim 6, further comprising an additional animal feed additive, wherein the additional animal feed additive is a nutritional feed additive, a general feed additive or a medicinal feed additive, and wherein the general feed additive is selected from growth promoters, deworming agents, flavoring, attractants, feed conditioning agents, feed conditioners, feed preservatives, and Chinese herbal medicine additives.

8. The feed composition according to claim 6, further comprising a feed raw material, wherein the feed raw material is selected from animal, plant, microbial and mineral non-feed-additive substances that are usable for preparing feed.

9. A method of preparing an animal feed additive comprising mixing the polyvalent metal ion compound salt of N,N-dimethylglycine and the organic acid of claim 1 or a solvate thereof with an auxiliary material usable for feed.

10. A method of preparing an animal feed comprising mixing the polyvalent metal ion compound salt of N,N-dimethylglycine and the organic acid of claim 1 or a solvate thereof with an auxiliary material usable for feed.

11. A method of preparing an animal feed additive comprising mixing the feed composition of claim 6 with an additional animal feed additive, wherein the additional animal feed additive is a nutritional feed additive, a general feed additive or a medicinal feed additive, and wherein the general feed additive is selected from growth promoters, deworming agents, flavoring, attractants, feed conditioning agents, feed conditioners, feed preservatives, and Chinese herbal medicine additives.

12. A method of preparing an animal feed comprising mixing the feed composition of claim 6 with an additional animal feed additive, wherein the additional animal feed additive is a nutritional feed additive, a general feed additive or a medicinal feed additive, and wherein the general feed additive is selected from growth promoters, deworming agents, flavoring, attractants, feed conditioning agents, feed conditioners, feed preservatives, and Chinese herbal medicine additives.

13. A feed composition, comprising at least one of the polyvalent metal ion compound salt of N,N-dimethylglycine and the organic acid of claim 5 or a solvate thereof and an auxiliary material usable for feed.

14. A method of preparing an animal feed additive comprising mixing the polyvalent metal ion compound salt of N,N-dimethylglycine and the organic acid of claim 5 or a solvate thereof with an auxiliary material usable for feed.

15. A method of preparing an animal feed comprising mixing the polyvalent metal ion compound salt of N,N-dimethylglycine and the organic acid of claim 5 or a solvate thereof with an auxiliary material usable for feed.

16. The feed composition according to claim 7, further comprising a feed raw material, wherein the feed raw material is selected from animal, plant, microbial and mineral non-feed-additive substances that are usable for preparing feed.

17. A method of preparing an animal feed additive comprising mixing the feed composition of claim 7 with a feed raw material, wherein the feed raw material is selected from animal, plant, microbial and mineral non-feed-additive substances that are usable for preparing feed.

18. A method of preparing an animal feed comprising mixing the feed composition of claim 7 with a feed raw material, wherein the feed raw material is selected from animal, plant, microbial and mineral non-feed-additive substances that are usable for preparing feed.

19. A method of preparing an animal feed additive comprising mixing the feed composition of claim 8 with an additional animal feed additive, wherein the additional animal feed additive is a nutritional feed additive, a general feed additive or a medicinal feed additive, and wherein the general feed additive is selected from growth promoters, deworming agents, flavoring, attractants, feed conditioning agents, feed conditioners, feed preservatives, and Chinese herbal medicine additives.

20. A method of preparing an animal feed comprising mixing the feed composition of claim 8 with an additional animal feed additive, wherein the additional animal feed additive is a nutritional feed additive, a general feed additive or a medicinal feed additive, and wherein the general feed additive is selected from growth promoters, deworming agents, flavoring, attractants, feed conditioning agents, feed conditioners, feed preservatives, and Chinese herbal medicine additives.

* * * * *